(12) United States Patent
Sander et al.

(10) Patent No.: US 9,045,412 B2
(45) Date of Patent: Jun. 2, 2015

(54) REACTIVE DISTILLATION PROCESS AND PLANT FOR OBTAINING ACETIC ACID AND ALCOHOL FROM THE HYDROLYSIS OF METHYL ACETATE

(71) Applicant: Sulzer Chemtech AG, Winterthur (SE)

(72) Inventors: Stefan Sander, Winterhur (SE); Laurent Zuber, Binningen (SE)

(73) Assignee: Sulzer Chemtech AG (CH)

( * ) Notice: Subject to any disclaimer, the term of this patent is extended or adjusted under 35 U.S.C. 154(b) by 0 days.

(21) Appl. No.: 14/283,167

(22) Filed: May 20, 2014

(65) Prior Publication Data

US 2014/0256985 A1  Sep. 11, 2014

Related U.S. Application Data

(62) Division of application No. 13/410,581, filed on Mar. 2, 2012.

(51) Int. Cl.

| C07C 29/80 | (2006.01) |
|---|---|
| C07C 51/09 | (2006.01) |
| C07C 51/487 | (2006.01) |
| B01D 3/00 | (2006.01) |
| B01D 3/14 | (2006.01) |
| C07C 51/44 | (2006.01) |
| C07C 29/09 | (2006.01) |
| C07C 29/147 | (2006.01) |
| C07C 29/88 | (2006.01) |

(52) U.S. Cl.
CPC .............. *C07C 51/487* (2013.01); *B01D 3/009* (2013.01); *B01D 3/141* (2013.01); *C07C 29/80* (2013.01); *C07C 51/09* (2013.01); *C07C 51/44* (2013.01); *C07C 29/095* (2013.01); *C07C 29/147* (2013.01); *C07C 29/88* (2013.01)

(58) Field of Classification Search
CPC .............................. C07C 29/095; C07C 51/09
USPC ......................................... 568/877; 562/608
See application file for complete search history.

(56) References Cited

U.S. PATENT DOCUMENTS

| 2,541,317 | A | 2/1951 | Wilson |
|---|---|---|---|
| 5,523,061 | A | 6/1996 | Hao et al. |
| 5,709,780 | A | 1/1998 | Ognisty et al. |
| 5,897,748 | A | 4/1999 | Kaibel |
| 6,348,637 | B1 | 2/2002 | Harris |
| 6,582,564 | B2 | 6/2003 | Tamura et al. |
| 7,041,199 | B1* | 5/2006 | Moritz et al. .................. 203/29 |
| 7,226,527 | B2 | 6/2007 | Bohner et al. |
| 7,329,774 | B2* | 2/2008 | Zuber et al. .................. 560/231 |
| 7,556,717 | B2 | 7/2009 | Heida |
| 7,619,126 | B2 | 11/2009 | Heida |
| 2003/0181772 | A1 | 9/2003 | Meyer et al. |
| 2004/0040829 | A1 | 3/2004 | Gall et al. |
| 2006/0135810 | A1 | 6/2006 | Wolfert et al. |
| 2008/0128262 | A1 | 6/2008 | Huang et al. |
| 2012/0245385 | A1 | 9/2012 | Sander et al. |

FOREIGN PATENT DOCUMENTS

| CN | 1042664 A | 6/1990 |
|---|---|---|
| CN | 1407960 A | 4/2003 |
| CN | 1433392 A | 7/2003 |
| CN | 1491196 A | 4/2004 |
| EP | 1 220 825 A2 | 7/2002 |
| EP | 1220825 B1 | 5/2003 |

OTHER PUBLICATIONS

Sander, S., et al., "Methyl Acetate Hydrolysis in a Reactive Divided Wall Column," Chemical Engineering Research and Design, vol. 85, No. 1, pp. 149-154, (Jan. 1, 2007) (2 pages).
Extended European Search Report from European Application No. 11159760.5 mailed Aug. 25, 2011 (5 pages).
Extended European Search Report from European Application No. 12155397.8 mailed Jun. 13, 2012 (4 pages).
Examination Report from European Application No. 12155397.8 mailed Apr. 24, 2013 (5 pages).

* cited by examiner

*Primary Examiner* — Sikarl Witherspoon
(74) *Attorney, Agent, or Firm* — Kilpatrick Townsend & Stockton LLP

(57) ABSTRACT

A method and plant for obtaining acetic acid and methanol from the hydrolysis of methyl acetate by reactive distillation is disclosed. The reactive distillation column is configured as a divided wall reactive distillation column (1). A feed containing water and methyl acetate are brought into contact with a catalyst in a reactive space (19) to perform the hydrolysis of water and methyl acetate to methanol and acetic acid. The reactive space comprises at least a first rectification zone (32), a first stripping zone (34) and a first reaction zone (33). A catalyst is provided in the first reaction zone (33). The column further comprises a product space (29) with at least a second rectification zone (42) and a second stripping zone (44). The second stripping zone (44) shares at least a portion of the column sump (38) with the first stripping zone (34). A first head product is discharged from a reactive space head portion (45) and a bottom product is discharged from the column sump (38) and a second head product is discharged from a product space head portion (46) and an intermediate product is discharged from the product space (29).

7 Claims, 2 Drawing Sheets

--PRIOR ART--

REACTIVE DISTILLATION PROCESS AND PLANT FOR OBTAINING ACETIC ACID AND ALCOHOL FROM THE HYDROLYSIS OF METHYL ACETATE

CROSS-REFERENCE TO RELATED APPLICATION

This application is a divisional of U.S. patent application Ser. No. 13/410,581 filed on Mar. 2, 2012, which claims benefit of European Patent Application No 11159760.5, filed on Mar. 25, 2011, the disclosures of which are hereby incorporated by reference.

The invention relates to a process and a plant for a reactive distillation for obtaining acetic acid and alcohol from the hydrolysis of methyl acetate. It is an important process in the production of polyvinyl acetate, during which methyl acetate is generated as a byproduct. The methyl acetate is transformed into acetic acid and methanol and is then fed back into the production process.

The hydrolysis of methyl acetate is often performed in a fixed bed reactor followed by several separation steps including distillation and extractive distillation. However, the yield of a fixed bed reactor is limited by the equilibrium of the chemical reaction, meaning that the conversion of methyl acetate to acetic acid and methanol will be completed only to the equilibrium point. Due to the fact that a substantial amount of methyl acetate and water remain unreacted in the fixed bed reactor as a consequence, large recycle streams have to be provided.

Therefore it has been considered to improve this process by providing a distillation column, in which a reaction section comprising structured packing, random packing or trays is provided for performing the reaction of a carboxylate to the corresponding carboxylic acid and alcohol. The reaction section of the column, in which the chemical reaction takes place, contains a heterogeneous catalyst, such as a structured packing of the KATAPAK™ type filled with Amberlyst type catalyst. Such reactive distillation plant and process for the hydrolysis of a carboxylate to obtain a carboxylic acid and alcohol has been disclosed in EP 1 220 825 B1. In the reaction section of the reactive distillation column it is possible to separate the reaction products, such as the carboxylic acid and the alcohol from the reactants, the carboxylates and water. This separation has the consequence that the stage of equilibrium for this chemical reaction is never reached and a yield of 100% is obtainable.

A disadvantage of the reactive distillation disclosed in the prior art is that all products and unconverted water exit the reactive distillation column via the sump and have to be separated subsequently in further separation columns. The head product of this reactive distillation column is only a small purge stream containing the carboxylate, alcohol and light boiling impurities. Because of the residence time in the sump and piping, reverse reactions are possible, which make it difficult to produce methyl-acetate-free methanol. A reverse reaction or back reaction occurs when the carboxylate is formed from the reaction products carboxylic acid and methanol. Thus the purity of products from such a reactive distillation column according to EP 1 220 825 B1 was inherently limited due to the required long residence time of the carboxylic acid and the alcohol in the sump and the subsequent heat exchangers before the carboxylic acid could finally be separated from the alcohol in a subsequent separation unit.

Therefore the process has been modified by combining the reactive distillation and the subsequent separation within one reactive divided wall column as disclosed in the article "Increased Purity at Reduced Costs" by Stefan Sander, published in the Sulzer Technical Review 1/2007 and in the article "Methyl Acetate Hydrolysis in a Reactive Divided Wall Column" by Stefan Sander et al., Trans IChemE, Chemical Engineering Research and Design, 2007, 85 (A1): 149-154.

However, the experimental data show, that even foreseeing a divided wall column as disclosed in the cited articles would lead to a prolonged residence time in the sump compared to EP 1 220 825 which promotes the occurrence of back reactions and the forming of methyl acetate. The experimental evidence shows that the reflux is about as large as five times the sum of the feed streams to the reactive distillation column.

Another problem encountered with the reactive divided wall column according to the article mentioned above relates to difficulties in controlling the product quality.

It is an object of the invention to design a method for the hydrolysis of methyl acetate in which the purity of the products methanol and/or acetic acid can be further increased.

The method for obtaining acetic acid and methanol from the hydrolysis of methyl acetate by reactive distillation according to the invention is performed in a reactive distillation column which is configured as a divided wall reactive distillation column including a column head, a column body and a column sump. The column body is arranged between the column head and the column sump.

The column comprises further a reactive space and a product space. The reactive space comprises at least a first rectification zone and a first reaction zone, whereby a hydrolysis catalyst is provided in the first reaction zone. The first rectification zone is arranged between the column head and the first reaction zone. The column further comprises a first stripping zone, with the first stripping zone being arranged between the column sump and the first reaction zone.

A feed containing water and methyl acetate enters the reactive space and is brought in contact with the hydrolysis catalyst to be at least partially hydrolysed to acetic acid and methanol. A first head product is discharged from a reactive space head portion. A bottom product is discharged from the column sump and a second head product is discharged from a product space head portion. An intermediate product is discharged from the product space.

Surprisingly, a more stable operation of the column is possible by an independent control of the reactive space and the product space if the intermediate product is discharged from the product space at the column body. Preferably the intermediate product is discharged at a position which between the top and the bottom of the divided wall. Therefore the side draw would only influence the flow conditions in the column in the product space thereof. Due to the presence of a divided wall, there is no influence on the flow conditions in the reactive space. Furthermore an intermediate product containing at least 99% methanol can be discharged.

It has been found, that the reactive space is also sensitive to liquid loading, therefore according to an advantageous embodiment, two condensers are provided. A first condenser performs the at least partial condensation of the head product of the reactive space and a second condenser performs the at least partial condensation of the head product of the product space. The first condenser can be operated and controlled independently from the second condenser. Thereby in independent control of the reactive space and the product space is possible.

In one embodiment a first feed containing at least 50% water and a second feed containing at least 15% methyl acetate enter the reactive space and are brought into contact with the hydrolysis catalyst to be at least partially hydrolysed to acetic acid and methanol and a first head product is discharged from a reactive space head portion and a bottom product is discharged from the column sump and a second head product is discharged from a product space head portion and an intermediate product is discharged from the product space, which contains at least 99% methanol.

The methanol, acetic acid and some of the methyl acetate and water leaving the reaction zone are separated further in the stripping zone. The stripping zone contains preferably at least one separation element, such as a structured packing, random packing or tray. The unreacted methyl acetate is pushed by the vapour ascending from the column sump back into the reaction zone, while the acetic acid, water and methanol flow into the direction of the column sump.

The vapour ascending from the column sump contains a high concentration of methanol and smaller amounts of water and acetic acid. This vapour is separated by the wall into two vapour parts, a first vapour part entering the reactive space, a second vapour part entering the product space of the divided wall column.

The product space comprises at least a second rectification zone and a second stripping zone. The second stripping zone shares at least a portion of the column sump with the first stripping zone. The second vapour part originating from the column sump entering the product space reaches first the second stripping zone and thereafter the second rectification zone. Each of the second stripping and rectification zones can contain at least one separation element, preferably a structured packing. In the second stripping zone, the methanol is separated from the acetic acid and water. Methanol is the lower boiling fraction compared to water and acetic acid, thus methanol leaves the column as intermediate product in an intermediate conduit. The intermediate conduit is positioned between the sump conduit and the second head discharge conduit. Acetic acid and water are the higher boiling fractions and are consequently discharged from the column sump via the sump conduit.

The light boiling fraction ascending through the second rectification zone contains methyl acetate and light boiling impurities. Any methanol carried into the second rectification zone can be separated by distillation to be added to the intermediate product. The second rectification zone may also contain at least one separation element, preferably a structured packing.

According to a particularly preferred embodiment of the method, the bottom product substantially consists of acetic acid and water, wherein the impurities in the bottom product can amount to less than 1%, preferably less than 0.5% particularly preferred less than 0.1%. All percentages relating to the amount of individual components in a flow, such as methyl acetate, methanol, water, acetic acid mentioned in this application are weight percentages.

According to a particularly preferred embodiment of the method, the second head product substantially consists of methanol and methyl acetate, wherein the impurities in the second head product amount to less than 1%, preferably less than 0.5% particularly preferred to less than 0.1%.

The back reaction, i.e. the formation of methyl acetate from methanol and acetic acid can occur in the reactive distillation column first stripping zone. The first stripping zone can comprise an upper separation element, such as a structured packing, random packing or tray, and a lower separation element, such as a structured packing, random packing or tray. The back reaction can take place in or on each of the upper or lower separation elements, here mainly in the upper part thereof and in the internals in between these two separation elements as well as in the bottom part of the methanol separation section in the product space. In all of these sections mentioned above, methanol and acetic acid occur in considerable amounts allowing the back reaction. The column can be designed in that way that the sump and the heat exchanger are nearly free of methanol, so nearly no back reaction can occur in the sump.

A part of the formed methyl acetate will be present in the product space of the reactive distillation column. In case methanol is taken out at the top of the product space, thus above the second rectification zone, all methyl acetate entering this section will be found in the methanol. In case methanol is taken out as side product, the contents of the methyl acetate in this stream is reduced. The main amount of methyl acetate is taken out as purge stream at the top of this section. The purge stream at the column head according to this variant contains only methanol and methyl acetate and can be recycled through the reactive space of the reactive distillation column. The flow rate of this purge stream is approximately 1% of the feed stream.

According to an advantageous variant of the method, a pre-reactor feed containing methyl acetate is firstly fed to a pre-reactor, in which the methyl acetate is brought into contact with a hydrolysis catalyst in the presence of water, by means of which the methyl acetate is partially decomposed into acetic acid and methanol and a pre-reactor product containing methyl acetate, acetic acid and methanol is discharged from the pre-reactor and is fed as the first feed into the reactive distillation column.

The catalyst is advantageously a hydrolysis catalyst configured as a heterogeneous catalyst. This heterogeneous catalyst is preferably an ion exchange catalyst such as Amberlyst 48 or Amberlyst 15.

Advantageously a bottom product is drawn off from the column sump, which substantially consists of acetic acid and water.

According to a particularly preferred embodiment, a first head product is drawn off from the reactive space at the reactive space column head portion and a second head product is drawn off from the product space at the product space column head portion, said second head product consisting substantially of methanol and methyl acetate.

A methyl acetate hydrolysis plant for performing the inventive method has the following characteristics: The methyl acetate hydrolysis plant according to the invention for obtaining acetic acid and methanol through the hydrolysis of methyl acetate by reactive distillation includes a divided wall reactive distillation column containing a column head, a column body and a column sump. The column body is arranged between the column head and the column sump. The column further comprises a reactive space and a product space. A wall is arranged in parallel to the longitudinal axis of the column, said wall dividing the column into the reactive space and the product space. The reactive space comprises at least a first rectification zone and a first reaction zone with a hydrolysis catalyst being provided in the first reaction zone. The first rectification zone is arranged between the column head and the first reaction zone. The column further comprises a first stripping zone, with the first stripping zone being arranged between the column sump and the first reaction zone. The product space comprises at least a second rectification zone and a second stripping zone. The second stripping zone shares at least a portion of the column sump with the first stripping zone.

Advantageously, the methyl acetate hydrolysis plant has a sump conduit for drawing off a bottom product from the column sump, said bottom product substantially consisting of acetic acid and water.

According to a preferred embodiment, the methyl acetate hydrolysis plant is equipped with a first head discharge conduit for drawing off a first head product from a reactive space column head portion and a second head discharge conduit for drawing off a second head product from the product space column head portion, said second head product consisting substantially of methanol and methyl acetate.

Therefore a first condenser can be foreseen for condensing a portion of said first head product and a second condenser can be foreseen for condensing a portion of said second head product.

Furthermore a first reflux conduit can be provided for recycling a portion of said first head product to the reactive space and a second reflux conduit can be provided for recycling a portion of said second head product to the product space.

In an embodiment, a first feed conduit for a first feed containing water and a second feed conduit for a second feed containing methyl acetate are provided to enter the column on the reactive space thereof.

According to a particularly preferred embodiment, a pre-reactor feed conduit for a pre-reactor feed containing methyl acetate and water to a pre-reactor is provided. The pre-reactor contains a hydrolysis catalyst, by means of which the methyl acetate is partially cleavable into acetic acid and methanol. A pre-reactor product containing methyl acetate, acetic acid and methanol from the pre-reactor is provided to be fed to the second feed conduit to the divided wall reactive distillation column.

A further advantage of the invention compared to known methods which employ a plurality of distillation columns involving large recycle streams is the reduction of such recycle streams. Thereby the energy consumption is reduced.

An advantage of the invention as compared to EP1 220 821 B1 is that higher purities of methanol are obtainable. The column can be operated in a more stable way due to the fact that the reactive space and the product space can be controlled independently. The methanol is discharged from the column in a side stream arranged in the divided wall section of the product space thereof, which results in a higher purity of the methanol. It had been found that methanol is present only in regions with a short residence time. If the methanol is thus extracted from the divided wall section of the product space, the residence time is short.

A disadvantage of the column of EP1 220 821 B1 is the higher sensitivity to longer residence times in the sump and the sump heat exchanger due to the fact that according to this disclosure, methanol was present in the sump.

Due to the fact that according to the invention, the methanol is removed as a side stream, it is surprisingly possible to avoid the presence of methanol in the sump, therefore avoid any back reactions which would have a negative influence on the product purity.

Therefore a structured packing or trays are used in the reaction zone of a methyl acetate hydrolysis plant of any one of the preceding embodiments.

In particular, the structured packing used in the reaction zone of the methyl acetate hydrolysis plant can comprise a hydrolysis catalyst provided on the surfaces of a structured packing whereby the hydrolysis catalyst can in particular form a structured catalyst packing.

In an embodiment, the structured catalyst packing used in the methyl acetate hydrolysis plant can comprise at least one retaining device. The retaining device can comprise at least one of a bag for solid catalyst material or a flow channel.

Figure 1:
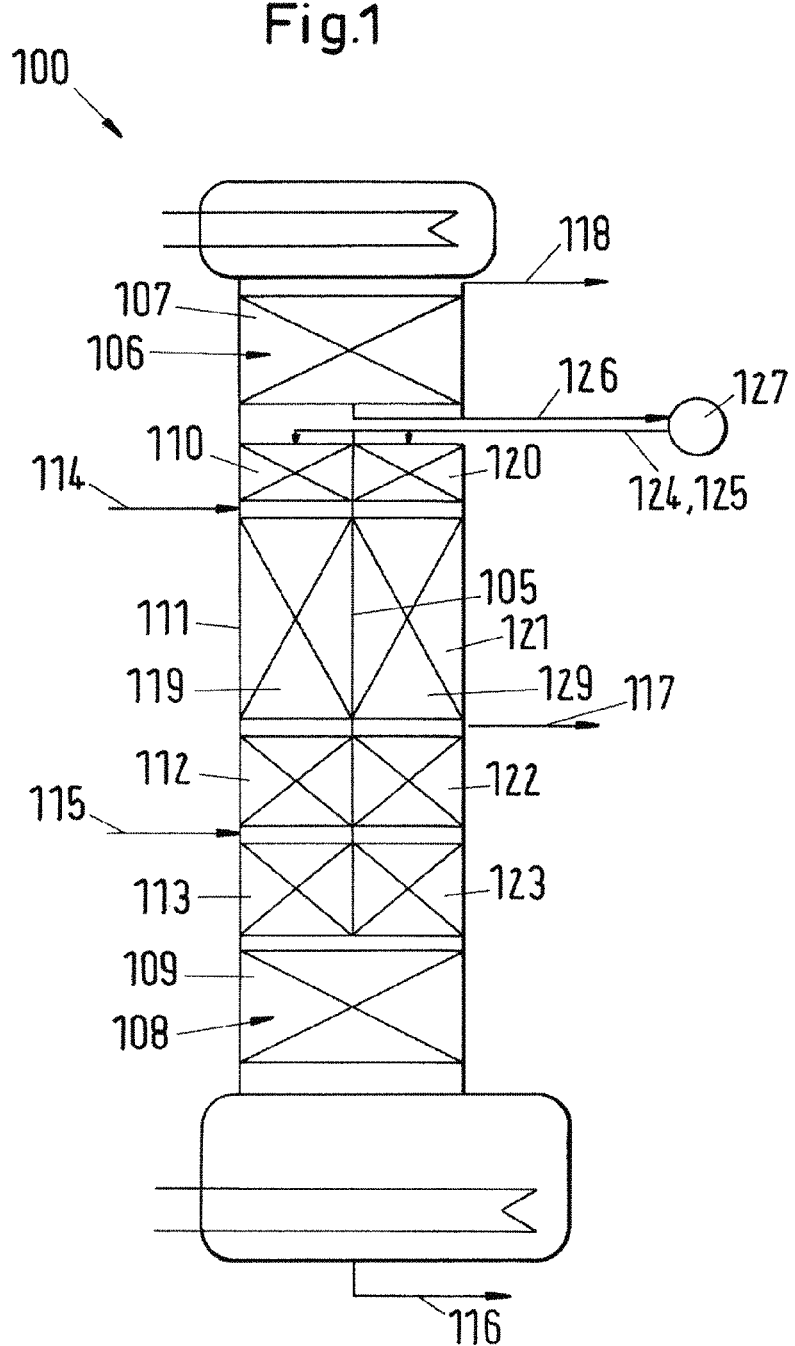
FIG. 1 shows a plant for performing the process according to the prior art.

According to FIG. 1 a reactive distillation column for the hydrolysis of methyl acetate to acetic acid and methanol is shown as disclosed in the articles cited in the introductory part of this application. This divided wall reactive distillation column 100 is of cylindrical shape having an inner diameter of 220 mm. The divided wall reactive distillation column comprises a wall 105 arranged vertically in the cylindrical portion thereof, dividing the inner space of the divided wall reactive distillation column in two partial spaces, a reactive space 119 and a product space 129. Each of these partial spaces contains at least one separation element. In the arrangement according to FIG. 1 the partial spaces are of the same size, thus the dividing wall divides the reactive distillation column into two halves.

The reactive space 119 on the feed side contains an uppermost separation element 110 which is a structured packing known as Sulzer MellapakPlus™ 752.Y, a first separation element 111 of structured catalyst packing known as Sulzer Katapak™-SP 11 arranged below the uppermost separation element 110, a second separation element 112 of Sulzer Katapak™-SP 11 arranged below the first separation element 111 and a lowermost separation element 113 consisting of Sulzer MellapakPlus™ 752.Y.

The product space 129 contains an uppermost separation element 120 which is a structured packing known as Sulzer MellapakPlus™ 752.Y, a first separation element 121 of Sulzer MellapakPlus™ 752.Y structured packing arranged below the uppermost separation element 120, a second separation element 122 consisting of Sulzer MellapakPlus™ 752.Y arranged below the first separation element 121 and a lowermost separation element 123 consisting of Sulzer MellapakPlus™ 752.Y.

The divided wall reactive distillation column 100 comprises furthermore a common head space 106 and a common sump space 108. The common head space 106 and the common sump space 108 both contain a separation element 107, 109 consisting of Sulzer MellapakPlus™ 752.Y structured packing. The total height of the packing section including collectors and distributors is 14.3 m. The collectors and distributors are not shown in the figures, a collector can be arranged below each of the separation elements 107, 109, 110, 111, 112, 113, 120, 121, 122, 123, a distributor can be arranged above each of the separation elements.

The feed entering the reactive space consists of two conduits, an upper feed conduit 114 for water and a lower feed conduit 115 for methyl acetate. The sump product leaves the column via the sump conduit 116, an intermediate product leaves the column via the intermediate conduit 117 and a head product leaves the column via the head conduit 118.

The liquid which is collected below the separation element 107 is drawn off from the separation element and directed by conduit 126 to the exterior of the column and fed into a splitter 127 for splitting the liquid into two reflux streams 124, 125. Each of the two reflux streams 124, 125 enters either the reactive space 119 or the product space 129.

In the column, the reactive distillation of methyl acetate was performed. The quantities and compositions of the process performed in the column as described above are laid down in table 1.

TABLE 1

| Stream name | Flow rate kg/h | Composition Weight % |
| --- | --- | --- |
| Feed 114, H$_2$O | 6.96 | 100% H$_2$O |
| Feed 115 Methyl acetate | 6.59 | 99.3% Methyl acetate |
| Product distillate 118 | 0.48 | 18.2% Methanol |
|  |  | 81.6% Methyl acetate |
| Product: intermediate 117 | 3.39 | 70.3% Methanol |
|  |  | 1.0% H$_2$O |
|  |  | 28.6% Methyl acetate |
| Product: sump 116 | 9.67 | 45.0% acetic acid |
|  |  | 55.0% H$_2$O |
| Reflux 124, 125 | 258.2 |  |

Figure 2:
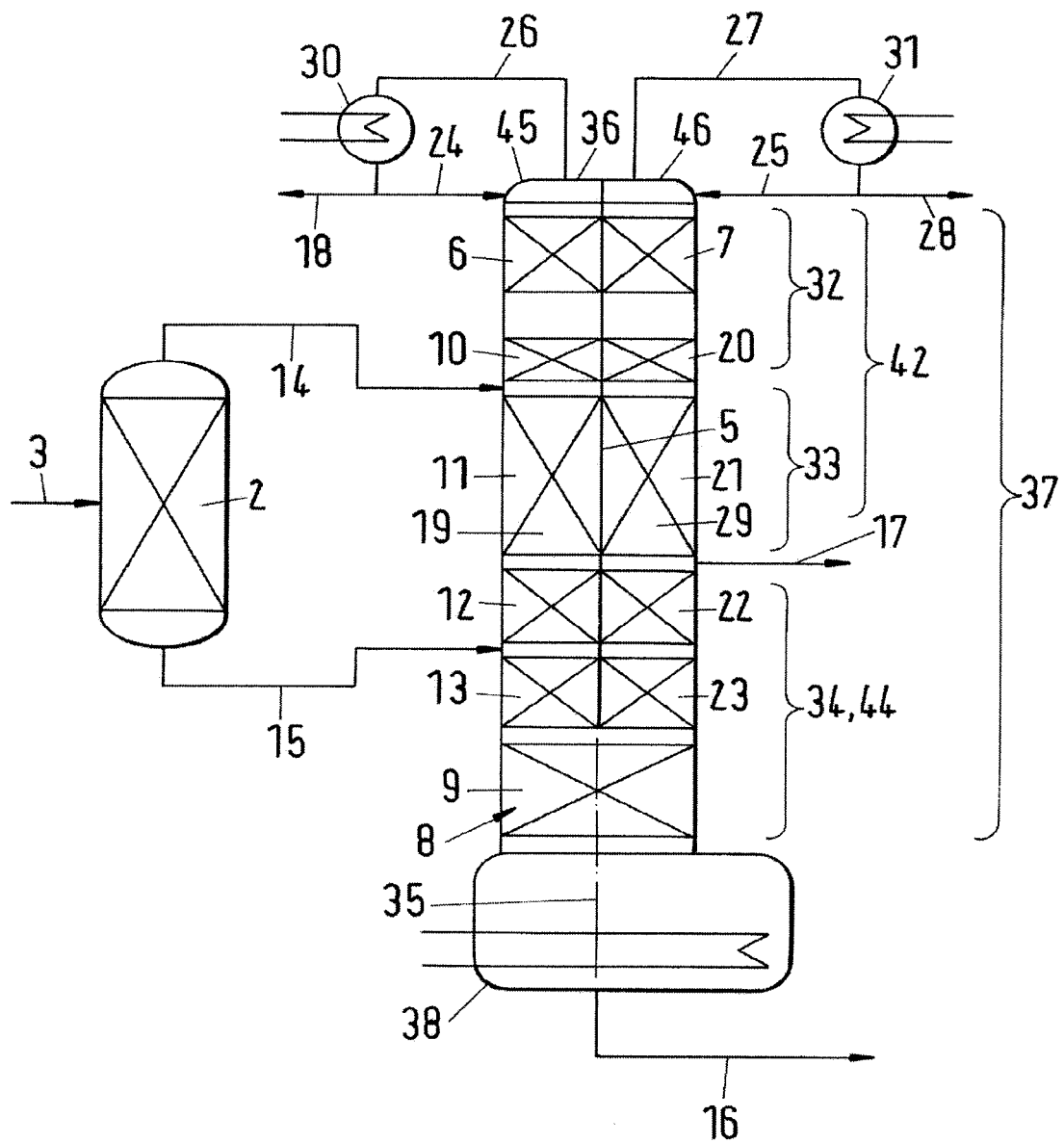
FIG. 2 shows a plant scheme for performing the hydrolysis of methyl acetate to acetic acid and water according to a particularly advantageous embodiment of the invention.

The methyl acetate hydrolysis plant according to the invention as shown in FIG. 2 for obtaining acetic acid and methanol through the hydrolysis of methyl acetate by reactive distillation includes a divided wall reactive distillation column 1 containing a column head 36, a column body 37 and a column sump 38. The column body 37 of the divided wall reactive distillation column 1 is of cylindrical shape. The column body 37 is arranged between the column head 36 and the column sump 38. The diameter of the column is around 1.6 m. The total height of the column is around 35 m.

The column comprises a reactive space 19 and a product space 29. A vertical wall 5 is arranged in parallel to the longitudinal axis 35 of the column. The wall 5 divides the column into the reactive space 19 and the product space 29. In FIG. 2 the wall extends vertically and divides the inner space into at least two partial spaces, namely the reactive space 19 and the product space 29. Each of these partial spaces contains at least one separation element. In the embodiment according to FIG. 2 the partial spaces are of the same size, thus the dividing wall 5 divides the reactive distillation column into two halves.

The reactive space 19 on the feed side contains an upper reactive head space separation element 6 and a lower reactive head space separation element 10, which are each configured as a structured packing known as Sulzer MellapakPlus™ 752.Y, a first separation element 11 consisting of structured catalyst packing Sulzer Katapak™-SP 11 arranged below the separation element 10, a second separation element 12 consisting of Sulzer Katapak™-SP 11 arranged below the first separation element 11 and a lowermost separation element 13 consisting of Sulzer MellapakPlus™ 752.Y.

The product space 29 contains an upper product head space separation element 7 and a lower product head space separation element 20, which are each configured as a structured packing known as Sulzer MellapakPlus™ 752.Y, a first separation element 21 consisting of Sulzer MellapakPlus™ 752.Y structured packing arranged below the lower product head space separation element 20, a second separation element 22 consisting of Sulzer MellapakPlus™ 752.Y arranged below the first separation element 21 and a lowermost separation element 23 consisting of Sulzer MellapakPlus™ 752.Y.

The reactive space 19 comprises at least a first rectification zone 32 and a first reaction zone 33 with a hydrolysis catalyst being provided in the first reaction zone 33. The hydrolysis catalyst is advantageously provided on the surfaces of a structured packing to form a structured catalyst packing.

Suitable structured catalyst packing types are described for example in U.S. Pat. No. 5,417,938 (Shelden), U.S. Pat. No. 5,470,542 (Stringaro), U.S. Pat. No. 5,536,699 Ghelfi), the content of which is hereby included by reference. The term structured catalyst packing should be understood to mean a structure having retaining devices, e.g. bags for solid catalyst material and having flow channels, which are present in the structure.

Structured packings are the preferred separation elements to carry out this invention. Suitable structured packing types include those disclosed in the documents cited above. Other separation elements that can be used to carry out the invention, which include random packing or trays, whereby a combination of structured packing, random packing or trays can be used as separation elements in the different zones.

In one embodiment the catalyst is present on the surface of such a structured packing, in another embodiment the catalyst is contained in bags arranged on the surface or within the body of the structured packing, between adjacent layers of a structured packing or in grooves formed in the layer of a sheet forming an element of such a structured packing. Other catalyst arrangements include catalyst arranged in bags with random packing or on trays.

The first rectification zone 32 is arranged between the column head 36 and the first reaction zone 33. The column further comprises a first stripping zone 34, with the first stripping zone 34 being arranged between the column sump 38 and the first reaction zone 33. The product space 29 comprises at least a second rectification zone 42 and a second stripping zone 44. The second stripping zone 44 shares at least a portion of the column sump 38 with the first stripping zone 34.

The divided wall reactive distillation column comprises thus a common sump space 8. The common sump space 8 contains a separation element 9 consisting of Sulzer MellapakPlus™ 752.Y structured packing. If the separation elements consist of structured packing, the complete arrangement of the separation elements in the column further includes collectors and distributors. The collectors and distributors are not shown in the figures, a collector can be arranged below each of the separation elements 6, 7, 9, 10, 11, 12, 13, 20, 21, 22, 23, a distributor can be arranged above each of these separation elements. A collector has the function of collecting the liquid flowing down the separation element arranged upstream with respect to the collector. A distributor has the function of distributing the liquid homogeneously over the separation element arranged downstream of the distributor.

The methyl acetate hydrolysis plant divided wall column has a sump conduit 16 for drawing off a bottom product from the column sump 38, said bottom product substantially consisting of acetic acid and water.

Furthermore the divided wall column of the methyl acetate hydrolysis plant is equipped with a first head discharge conduit 18 for drawing off a first head product from a reactive space column head portion 45 and a second head discharge conduit 28 for drawing off a second head product from the product space column head portion 46, said second head product consisting substantially of methanol and methyl-acetate. The head product vapors accumulate in the reactive space column head portion 45 and in the product space column head portion 46. They are discharged from the column head in discharge conduits 26, 27. A first condenser 30 is foreseen for condensing a portion of said first head product and a second condenser 31 is foreseen for condensing a portion of said second head product. A portion of the condensed vapor is recycled as a reflux stream in a first or second reflux conduit 24, 25 into the column at a position above the respective separation element 6, 7.

Thus the first reflux conduit 24 is provided for recycling a portion of said first head product to the reactive space 19 and the second reflux conduit 24 is provided for recycling a portion of said second head product to the product space 29.

In an embodiment, a first feed conduit 14 for a first feed containing water and a second feed conduit 15 for a second feed containing methyl acetate are provided to enter the column 1 on the reactive space 19 thereof.

According to a particularly preferred embodiment, a pre-reactor feed conduit 3 for a pre-reactor feed containing methyl acetate and water to a pre-reactor 2 is provided. The pre-reactor 2 contains a hydrolysis catalyst, by means of which the methyl acetate is partially decomposable into acetic acid and methanol. A pre-reactor product containing methyl acetate, acetic acid and methanol from the pre-reactor is provided to be fed to the feed conduit 14 to the divided wall reactive distillation column 1.

In the column, the reactive distillation of methyl acetate was simulated using Pro/II™ process simulation software from SimSci (Invensys). The quantities and compositions of the process performed in the column as described above are laid down in table 2.

TABLE 2

| Stream name | Flow rate Kg/h | Composition Weight % |
|---|---|---|
| Feed 14, $H_2O$ | 9500.0 | 10% Methanol |
| | | 19% Acetic acid |
| | | 52% $H_2O$ |
| | | 19% Methyl acetate |
| Product: distillate 18 | 5 | 13.4% Methanol |
| | | 0% Acetic acid |
| | | 0.4% $H_2O$ |
| | | 86.2% Methyl acetate |
| Product: distillate 28 | 31.2 | 62.9% Methanol |
| | | 0% Acetic acid |
| | | 0% $H_2O$ |
| | | 37.1% Methyl acetate |
| Product: intermediate 17 | 1697.9 | 99.8% Methanol |
| | | 0% Acetic acid |
| | | 0.1% $H_2O$ |
| | | 0.1% Methyl acetate |
| Product: sump 16 | 7776.3 | 0.2% Methanol |
| | | 41.9% Acetic acid |
| | | 57.9% $H_2O$ |
| | | 0% Methyl acetate |

The method for obtaining acetic acid and methanol from the hydrolysis of methyl acetate by reactive distillation according to the invention comprises the following steps: a first feed containing at least 50% water and a second feed containing at least 15% methyl acetate are brought into contact with a hydrolysis catalyst in a reactive distillation column by means of which the methyl acetate is at least partially hydrolysed to acetic acid and methanol. The resulting reaction mixture is simultaneously separated at least partially into the components acetic acid and methanol. The first and second feed streams enter the reactive space 19 of the column to perform the hydrolysis of water and methyl acetate to methanol and acetic acid and a first head product is discharged from a reactive space head portion 45 and a bottom product is discharged from the column sump 38 and a second head product is discharged from a product space head portion 46 and an intermediate product is discharged from the product space 29, which contains at least 99% methanol.

According to table 2 the purity of the intermediate product 17 reached was 99.8% compared to the purity of the intermediate product 117 of 70.3% according to table 1.

The intermediate product helps to separate methanol from acetic acid immediately after completion of the chemical reaction in the reaction zone 33. Thereby a prolonged contact between methanol and acetic acid is avoided. Therefore the possibility for a back reaction is greatly reduced due to the fact that the reaction products methanol and acetic acid are separated by distillation in the product space 29 of the divided wall column.

For the various example conditions here and in the prior art as disclosed in the cited article, surprisingly in addition to the increased purity of the intermediate product, the calculated data as disclosed in table 2 reveal that the sum of the feed streams is in the same order of magnitude as the sum of the recycled portions of the first and second head products, which is about 9570 kg/hr. This means not only that the residence time of the components in the column is considerably reduced compared to the prior art, it also means that the energy consumption of the method according to the invention is considerably lower. Compared to the solution according to table 1 the energy consumption could be as low as ⅕ due to the fact that the recycle streams of the method according to table 1 are about five times larger than the recycle streams of the experimental set up as shown in table 2.

A pre-reactor feed containing methyl acetate is firstly fed to a pre-reactor 2, in which the methyl acetate is brought into contact with a hydrolysis catalyst in the presence of water, by means of which the methyl acetate is partially cleaved into acetic acid and methanol and a pre-reactor product containing methyl acetate, acetic acid and methanol is discharged from the pre-reactor 2 and is fed as the first feed into the reactive distillation column.

The bottom product drawn off from the column sump substantially consists of acetic acid and water. A first head product is drawn off from the reactive space 19 at the reactive space column head portion 45 and a second head product is drawn off from the product space 29 at the product space column head portion 46, said second head product consisting substantially of methanol and methyl acetate.

The invention claimed is:
1. A method for obtaining acetic acid and methanol from the hydrolysis of methyl acetate by reactive distillation in a reactive distillation column having a pre-reactor, the reactive distillation column being configured as a divided wall reactive distillation column including a column head, a column body, a first reflux conduit, a second reflux conduit, and a column sump with the column body being arranged between the column head and the column sump, the column further comprising a wall arranged in parallel to the longitudinal axis of the column, said wall dividing the column into a reactive space and a product space, wherein the reactive space comprises at least a first rectification zone and a first reaction zone, with a hydrolysis catalyst provided in the first reaction zone, and the first rectification zone is arranged between the column head and the first reaction zone, the column further comprising a first stripping zone, with the first stripping zone being arranged between the column sump and the first reaction zone, wherein the product space comprises at least a second rectification zone and a second stripping zone, wherein the second stripping zone shares at least a portion of the column sump with the first stripping zone, the method comprising: providing a pre-reactor feed containing methyl acetate to a pre-reactor, discharging a first feed containing water and methyl acetate from the pre-reactor to the reactive distillation column, providing the first feed containing water and methyl acetate to the reactive space, bringing the feed into contact with the hydrolysis catalyst, at least partially hydrolysing the feed to acetic acid and methanol, discharging a first head product from a reactive space head portion, recycling a portion of the first head product via the first reflux conduit to the reactive space, discharging a bottom product from the column sump, discharging a second head product from a product space head portion, recycling a portion of the second head product via the second reflux conduit to the product space, and discharging an intermediate product from the product space.

2. The method of claim 1, wherein when the pre-reactor feed containing methyl acetate is fed to the pre-reactor, the methyl acetate is brought into contact with a hydrolysis catalyst in the presence of water, by which the methyl acetate is partially cleaved into acetic acid and methanol and a pre-reactor product containing methyl acetate, acetic acid, and methanol is discharged from the pre-reactor and is fed as the first feed into the reactive distillation column.

3. The method of claim 1, further comprising providing the first feed containing at least 50 wt % water and a second feed containing at least 15 wt % methyl acetate to enter the reactive space and bringing the first feed into contact with the hydrolysis catalyst to be at least partially hydrolysed to acetic acid and methanol, and discharging a first head product from a reactive space head portion, discharging a bottom product from the column sump, discharging a second head product from a product space head portion, and discharging an intermediate product is discharged from the product space, which contains at least 99 wt % methanol.

4. The method of claim 1, wherein the methanol and methyl acetate in the bottom product amount to less than 1% of the bottom product.

5. The method of claim 4, wherein the methanol and methyl acetate in the bottom product amount to less than 0.5% of the bottom product.

6. The method of claim 5, wherein the methanol and methyl acetate in the bottom product amount to less than 0.1% of the bottom product.

7. The method of claim 1, further comprising condensing a portion of each of the first head product and the second head product for recycling.

* * * * *

UNITED STATES PATENT AND TRADEMARK OFFICE
CERTIFICATE OF CORRECTION

PATENT NO. : 9,045,412 B2  
APPLICATION NO. : 14/283167  
DATED : June 2, 2015  
INVENTOR(S) : Stefan Sander and Laurent Zuber It is certified that error appears in the above-identified patent and that said Letters Patent is hereby corrected as shown below:

On the title page, page 1, column 1, insert

-- (30)    Foreign Application Priority Data  
    Mar. 25, 2011     (EP) ....................... 11 159 760.5 --

Signed and Sealed this  
Twelfth Day of January, 2016

Michelle K. Lee  
*Director of the United States Patent and Trademark Office*